US009194727B2

(12) United States Patent
Young et al.

(10) Patent No.: US 9,194,727 B2
(45) Date of Patent: Nov. 24, 2015

(54) MECHANICAL TESTING INSTRUMENTS INCLUDING ONBOARD DATA

(75) Inventors: Christopher David Young, Excelsior, MN (US); Daniel Paul Carlson, Coon Rapids, MN (US); Lucas Paul Keranen, Hutchinson, MN (US); Jeffrey P. Schirer, Minnetonka, MN (US)

(73) Assignee: Hysitron, Inc., Eden Prairie, MN (US)

( * ) Notice: Subject to any disclaimer, the term of this patent is extended or adjusted under 35 U.S.C. 154(b) by 0 days.

(21) Appl. No.: 13/989,383

(22) PCT Filed: Nov. 23, 2011

(86) PCT No.: PCT/US2011/062129
§ 371 (c)(1),
(2), (4) Date: Aug. 12, 2013

(87) PCT Pub. No.: WO2012/071560
PCT Pub. Date: May 31, 2012

(65) Prior Publication Data
US 2013/0332100 A1 Dec. 12, 2013

Related U.S. Application Data

(60) Provisional application No. 61/417,134, filed on Nov. 24, 2010.

(51) Int. Cl.
*G01D 18/00* (2006.01)
*B82Y 35/00* (2011.01)
(Continued)

(52) U.S. Cl.
CPC .............. *G01D 18/008* (2013.01); *B82Y 35/00* (2013.01); *G01B 5/28* (2013.01); *G01B 21/042* (2013.01);
(Continued)

(58) Field of Classification Search
CPC ............................ G05B 19/404; G01D 18/008
USPC ......................................................... 702/105
See application file for complete search history.

(56) References Cited

U.S. PATENT DOCUMENTS

| 4,694,687 A | 9/1987 | Bonin et al. | |
| 5,406,832 A * | 4/1995 | Gamble et al. | 73/105 |

(Continued)

FOREIGN PATENT DOCUMENTS

| EP | 1632767 A2 | 3/2006 |
| EP | 2028439 A1 | 2/2009 |

(Continued)

OTHER PUBLICATIONS

"International Application Serial No. PCT/US/2011/062129, Search Report mailed Apr. 2, 2012", 2 pgs.

(Continued)

*Primary Examiner* — Patrick Assouad
*Assistant Examiner* — Haidong Zhang
(74) *Attorney, Agent, or Firm* — Schwegman Lundberg & Woessner, P.A.

(57) ABSTRACT

A method of calibrating a mechanical instrument assembly includes reading a memory device coupled with a mechanical testing instrument, the mechanical testing instrument having one or more mechanical characteristics with values unique to the mechanical testing instrument, and reading includes reading of one or more calibration values based on the one or more mechanical characteristic values. The method further includes calibrating the mechanical instrument assembly according to the one or more calibration values. The mechanical testing instrument is coupled with the mechanical instrument assembly.

25 Claims, 8 Drawing Sheets

(51) Int. Cl.
  *G01B 5/28* (2006.01)
  *G01B 21/04* (2006.01)
  *G01N 1/42* (2006.01)
  *G01Q 60/36* (2010.01)
  *G01Q 40/00* (2010.01)
  *G01Q 30/04* (2010.01)

(52) U.S. Cl.
  CPC ............... *G01N 1/42* (2013.01); *G01Q 30/04* (2013.01); *G01Q 40/00* (2013.01); *G01Q 60/366* (2013.01); *G01N 2203/021* (2013.01); *G01N 2203/0206* (2013.01)

(56) References Cited

U.S. PATENT DOCUMENTS

| | | | |
|---|---|---|---|
| 5,576,483 | A | 11/1996 | Bonin |
| 5,753,911 | A | 5/1998 | Yasuda et al. |
| 5,869,751 | A * | 2/1999 | Bonin ........................ 73/105 |
| 5,877,497 | A | 3/1999 | Binnig et al. |
| 6,163,519 | A * | 12/2000 | Kuroda et al. ............... 369/126 |
| 7,516,035 | B2 | 4/2009 | Tellenbach et al. |
| 2003/0025498 | A1 * | 2/2003 | Imai et al. .................... 324/244 |
| 2006/0000263 | A1 * | 1/2006 | Su et al. ........................ 73/105 |
| 2007/0107502 | A1 | 5/2007 | Degertekin |
| 2008/0011064 | A1 | 1/2008 | Masser et al. |
| 2008/0121028 | A1 | 5/2008 | Kley |
| 2010/0095780 | A1 * | 4/2010 | Oh et al. ........................ 73/774 |
| 2010/0268503 | A1 | 10/2010 | Specht et al. |

FOREIGN PATENT DOCUMENTS

| | | |
|---|---|---|
| WO | WO-2010003154 A1 | 1/2010 |
| WO | WO-2010132441 A1 | 6/2010 |
| WO | WO-2012/071560 A1 | 5/2012 |

OTHER PUBLICATIONS

"International Application Serial No. PCT/US2011/062129, International Preliminary Report on Patentability mailed Feb. 5, 2013", 27 pgs.

"International Application Serial No. PCT/US2011/062129, Written Opinion mailed Apr. 2, 2012", 8 pgs.

"European Application Serial No. 11843619.5, Extended European Search Report mailed Apr. 22, 2014", 7 pgs.

"International Application Serial No. PCT/US2011/062129, Demand and Response filed Sep. 24, 2012 to Written Opinion mailed Apr. 2, 2012", 27 pgs.

"European Application Serial No. 11843619.5, Examination Notification Art. 94(3) mailed Feb. 11, 2015", 4 pgs.

Response/Amendment filed Jun. 17, 2015 in response to Examination Notification Article 94(3) EPC filed in EP Application Serial No. 118443619.5, filed Nov. 23, 2011, 14 pgs.

* cited by examiner

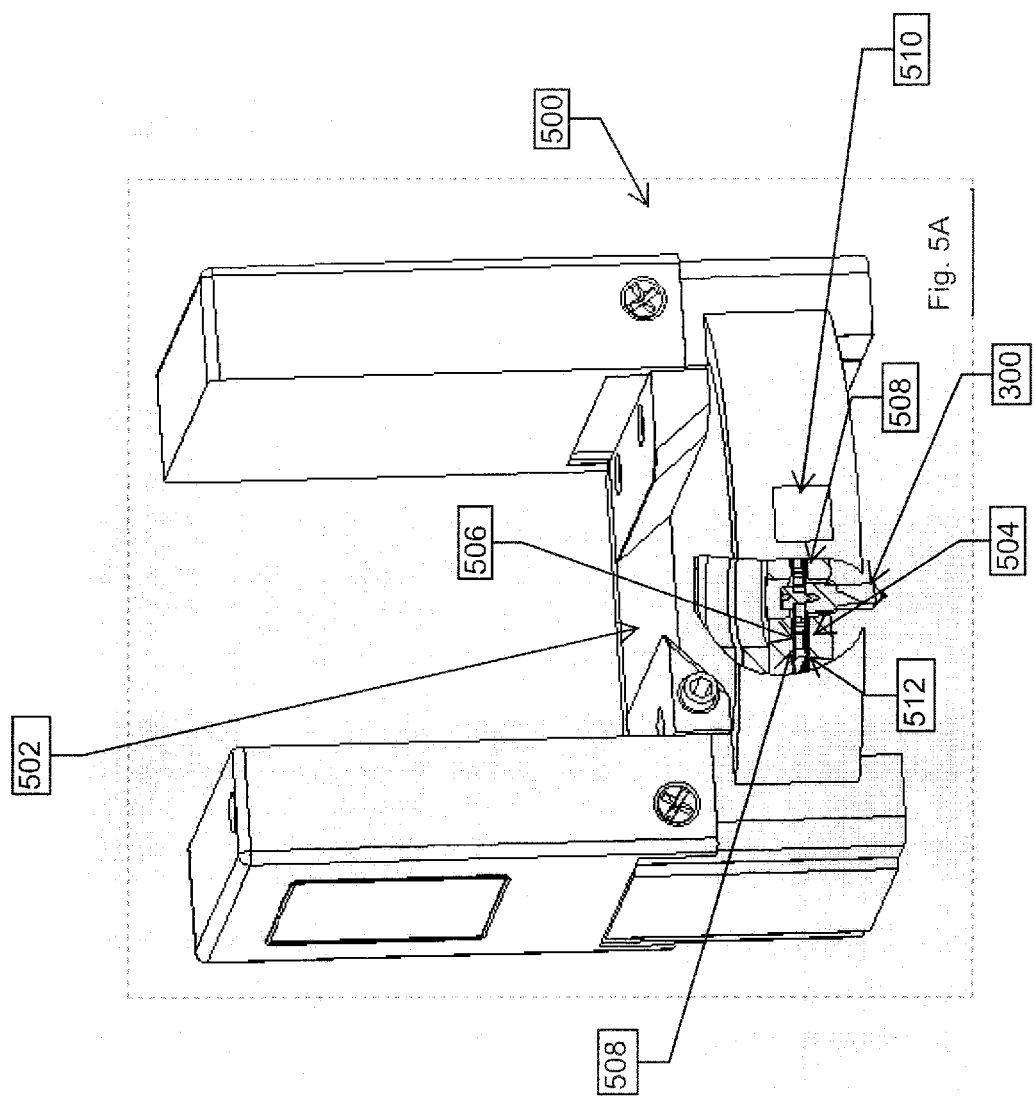

MECHANICAL TESTING INSTRUMENTS INCLUDING ONBOARD DATA

RELATED APPLICATIONS

This application is a U.S. National Stage Filing from International Patent Application Serial No. PCT/US2011/062129, filed Nov. 23, 2011, and published on May 31, 2012 as WO 2012/071560, which claims the priority benefit of U.S. Provisional Application Ser. No. 61/417,134, filed Nov. 24, 2010, the contents of which applications and publication are incorporated herein by reference in their entirety.

TECHNICAL FIELD

Mechanical property testing at a micron scale or smaller.

BACKGROUND

Mechanical testing instruments including transducers, tips and the like are constructed according to industry standards for the respective components, machines utilizing those components, testing methods and the like. Mechanical characteristics, such as tip shapes, spring constants and the like for mechanical testing instruments are used in calculations to determine mechanical parameters of samples from measurements taken with mechanical testing instruments. The mechanical characteristics are input into machines for instance from product literature, databases and the like.

Errors sometimes occur where information on these mechanical characteristics is improperly entered from literature or databases. Additionally, incorrect transducers, tips and the like (mechanical testing instruments) are installed in machines with resulting errors in measurement that are difficult to track to the incorrectly installed mechanical testing instruments. In some examples, time consuming analysis is needed to determine an improper mechanical testing instrument is installed. In other examples, blame for the error is improperly assessed to another component and the otherwise properly installed component is unnecessarily replaced or serviced while the incorrectly installed mechanical testing instrument remains in service.

DESCRIPTION OF THE DRAWINGS

In the following detailed description, reference is made to the accompanying drawings which form a part hereof, and in which is shown by way of illustration specific examples in which the subject matter may be practiced. These examples are described in sufficient detail to enable those skilled in the art to practice the subject matter, and it is to be understood that other examples may be utilized and that structural changes may be made without departing from the scope of the present subject matter. Therefore, the following detailed description is not to be taken in a limiting sense, and the scope of the present subject matter is defined by the appended claims and their equivalents.

FIG. 5A is a perspective and partial cross sectional view of one example of a transducer assembly for use with the mechanical instrument assembly shown in FIG. 2.

Figure 1:
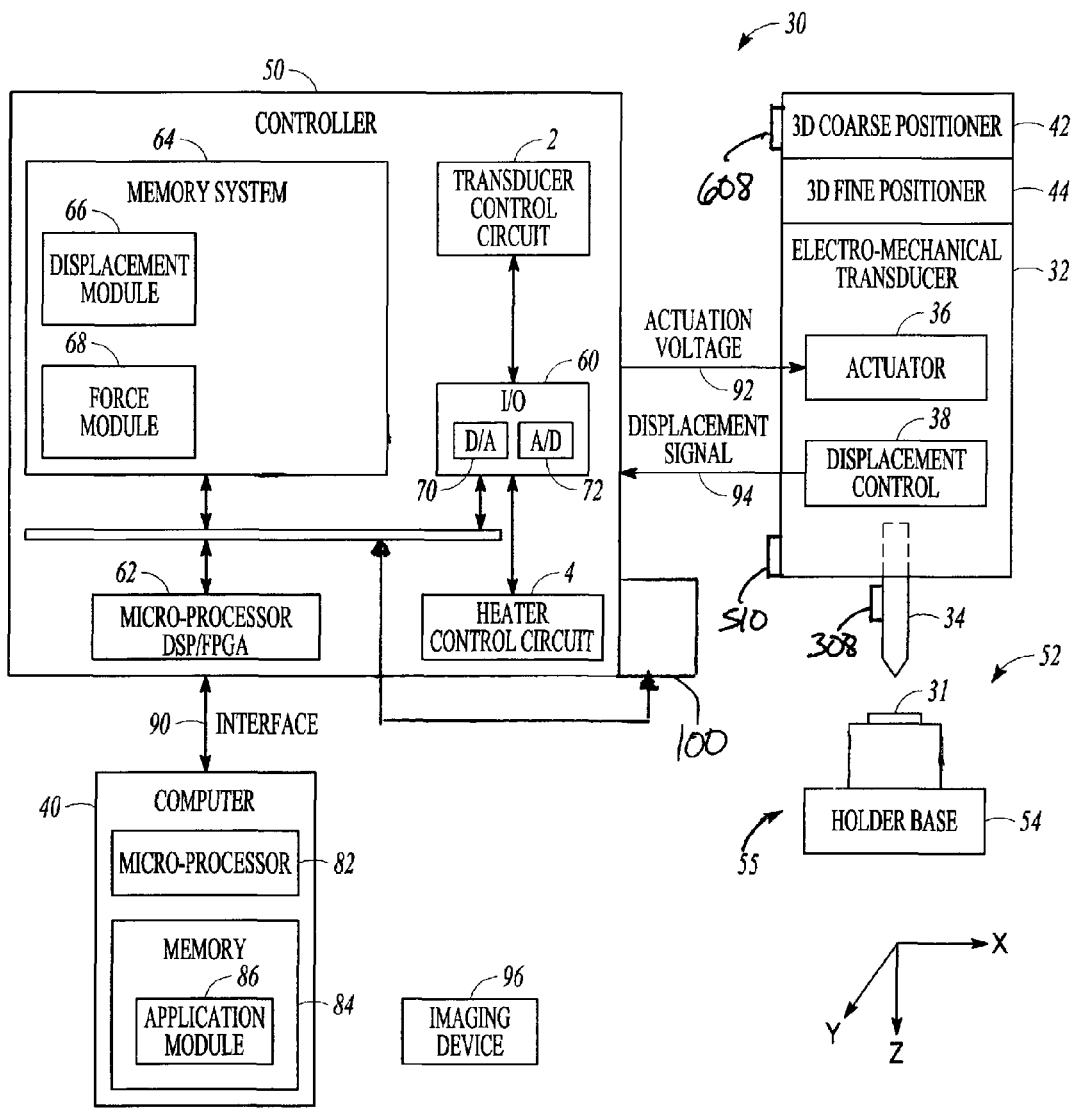
FIG. 1 is a block diagram showing one example of a nanomechanical test system.

The present subject matter may be described in terms of functional block components and various processing steps. Such functional blocks may be realized by any number of techniques, technologies, and methods configured to perform the specified functions and achieve the various results. The systems described are merely exemplary applications.

DESCRIPTION OF THE DRAWINGS

In the following detailed description, reference is made to the accompanying drawings which form a part hereof, and in which is shown by way of illustration specific examples in which the subject matter may be practiced. These examples are described in sufficient detail to enable those skilled in the art to practice the subject matter, and it is to be understood that other examples may be utilized and that structural changes may be made without departing from the scope of the present subject matter. Therefore, the following detailed description is not to be taken in a limiting sense, and the scope of the present subject matter is defined by the appended claims and their equivalents.

The present subject matter may be described in terms of functional block components and various processing steps. Such functional blocks may be realized by any number of techniques, technologies, and methods configured to perform the specified functions and achieve the various results. The present subject matter may be practiced in conjunction with any number of devices, and the systems described are merely exemplary applications.

As used herein, the terms "comprises", "comprising", or any variation thereof, are intended to reference a non-exclusive inclusion, such that a process, method, article, composition or apparatus that comprises a list of elements does not include only those elements recited, but may also include other elements not expressly listed or inherent to such process, method, article, composition or apparatus. Other combinations and/or modifications of the above-described structures, arrangements, applications, proportions, elements, materials or components used in the practice of the present subject matter, in addition to those not specifically recited, may be varied or otherwise particularly adapted to specific environments, manufacturing specifications, design parameters or other operating requirements without departing from the general principles of the same.

In the following detailed description, reference is made to the accompanying drawings which form a part hereof, and in which is shown by way of illustration how specific embodiments of the present disclosure may be practiced. In this regard, directional terminology, such as "top," "bottom," "front," "back," "leading," "trailing," etc., is used with reference to the orientation of the Figure(s) being described. Because components of embodiments of the present invention can be positioned in a number of different orientations, the directional terminology is used for purposes of illustration and is in no way limiting. These embodiments are described in sufficient detail to enable those skilled in the art to practice aspects of this disclosure, and it is to be understood that other embodiments may be utilized and that structural changes may be made without departing from the scope of the present disclosure. Therefore, the following detailed description is not to be taken in a limiting sense, and the scope of the present disclosure is defined by the appended claims and their equivalents.

According to embodiments described herein, a system and method are provided for mechanically testing small test subjects at the nano and micro scales (i.e., sub-micron scale), including, but not limited to, nanostructures, thin films and the like. Such testing is performed, in one example, to determine the mechanical properties of the materials composing the subjects. The systems and methods described herein form or are parts of an instrument which provides a high precision actuation force, corresponding indenting or other deformation (e.g., indenting, scratching, pulling, compressing and the like), and high resolution displacement sensing, scanning and imaging on at least a nanometer or micrometer scale.

FIG. 1 is a schematic block diagram illustrating an example of a nanomechanical test system 30. The nanomechanical test system 30 (e.g., sub-micron scale testing) includes an electromechanical or electro-magnetic (EM) transducer 32 having a displaceable probe 34, an actuator 36 to displace the probe 34, a displacement sensor 38, a computer 40, a coarse positioner 42, a fine positioner 44, and a controller 50. The EM transducer 32 includes, but is not limited to, indentation, compression, tensile, fatigue, tribology, fracture instruments and the like.

The nanomechanical test system 30 further includes a test subject holder 55 including a sample stage 52 having a base portion 54 (a holder base). The test subject holder 55 is detachably mounted to the nanomechanical test system 30.

According to one embodiment, the controller 50 includes an input/output module 60, a transducer control circuit 2, a processor 62, such as a microprocessor or digital signal processor (DSP) and/or field programmable gate array (FPGA), and a memory system 64. According to another embodiment, the memory system 64 includes a displacement module 66, a force module 68. According to another embodiment, the input/output module 60 further includes a D/A converter 70, and an A/D converter 72.

In one example, the computer 40 includes a processor 82 and a memory system 84 that stores an application module 86. The computer 40 may access and communicate with the controller 50 via an interface 90 (e.g. a USB interface). FIG. 1 shows the computer 40 and controller 50 as separate entities. In other examples, the computer 40 and controller 50 are combined as part of a single processing and control system.

According to one embodiment, the application module 86, the displacement module 66, and the force module 68 each include instructions respectively stored in memories 64 and 84 and which are accessible and executable by the processor 62. The memories 64 and 84 include, but are not limited to, any number of volatile or non-volatile storage devices such as RAM, flash memory, hard disk drives, CD-ROM drives, DVD drives and the like. In other embodiments, the displacement module 66 and the force module 68 include any combination of hardware and software components configured to perform functions described herein. The software components of the displacement module 66 and the force module 68 are each stored on a medium separate from the processing system 62 prior to being stored in the memory system 64, in one example. Examples of such media include a hard disk drive, a flash memory device, a compact disc (e.g. a CD-ROM, CD-R, or CD-RW), and a digital video disc (e.g. a DVD, DVD-R, and DVD-RW), for example.

According to one embodiment, the coarse positioner 42 and the fine positioner 44 enable 3-dimensional positioning (i.e. x-, y-, and z-axes in FIG. 1) of the EM transducer 32 and the displaceable probe 34 in the millimeter range with a sub-nanometer resolution. According to one embodiment, final positioning and movement of the displaceable probe 34 is performed by the actuator 36 via the application module 86 on the computer 40 and the controller 50. According to one embodiment, the controller 50 is configured to control and monitor the movement of displaceable probe 34 and to provide data representative of a displacement of the displaceable probe 34 (from the displacement sensor as part of the displacement control 38) to the computer 40 through the interface 90. According to one embodiment, the controller 50 is configured to determine and adjust a force applied to the test sample 31 by the displaceable probe 34.

In operation, a user can program the controller 50 with the computer 40 through the application module 86. According to one embodiment, the controller 50, through the force module 68, provides an input or force signal 92 to the actuator 36 representative of a desired force for application to the test sample 31 by the displaceable probe 34. In response to the input actuation force signal 92, the actuator 36 drives the displaceable probe 34 toward the sample stage 52 (e.g. along the z-axis in FIG. 1). The displaceable probe 34 contacts and applies the desired force to the test subject 31. The D/A converter 70 converts the input or force signal provided by the force module 68 from digital to analog form which, in turn, is amplified to generate the actuation force 92 by the transducer control circuit 2 as provided to actuator 36.

The displacement sensor 38 comprises a transducer (e.g. a capacitive transducer) which detects movement of displaceable probe 34 at least along the z-axis (and the x-y axes in some examples), and provides a displacement signal 94 to the controller 50 representing measurement of the movement of the displaceable probe 34. In other embodiments, in addition to movement along the z-axis, the displacement sensor 38 detects and provides indication of other types of movement of the displaceable probe 34, such as displacement along the x- and/or y-axes or rotational movement about the x- and/or y-axes. The transducer control circuit 2 conditions the displacement signal 94 from the displacement sensor 38 and sends the displacement signal 94 to the A/D converter 72. The A/D converter 72 converts the displacement signal 94 from an analog form, as received from the transducer control circuit 2, to a digital form for processing by the displacement module 66. The displacement module 66, according to one embodiment, communicates measurement of the movement of the displaceable probe 34 to the force module 68 (e.g. for force calculations) and the computer 40 (via interface 90).

According to one embodiment, the controller 50 is further configured to control movement or displacement of displaceable probe 34 in the x- and y-directions relative to sample stage 52, such as by moving EM transducer 32 relative to sample stage 52 or by moving sample stage 52 relative to EM transducer 32. According to one embodiment, the nanomechanical test system 30 further includes an imaging device 96 comprising an instrument/device such as an electron microscope, an optical microscope, or a scanning probe microscope (SPM) (e.g., an atomic force microscope (AFM)) configured to provide images of a test sample 31 mounted to sample stage 52, including images of the test subject before, during and after mechanical testing such as indentation, compression, fatigue and fracture testing and the like and video of the same.

The nanomechanical test system 30 further includes a reader 100 configured to read one or more memory devices as described herein. In one example, the reader 100 includes one or more of electrical contacts, a radio frequency transmitter and receiver, optical bar code reader, optical instrument and the like configured to interact with a corresponding memory device (e.g., data storage or containing device) 308, 510, 608 coupled with a mechanical instrument assembly including, but not limited to, a probe tip, transducer assembly, imaging scanner assembly and the like. In the example shown in FIG. 1, the memory device 608 is coupled with the EM Transducer 32 including for instance the instrument configured to receive the transducer assembly 500 described herein. Optionally or in addition to the EM Transducer 32, the memory device 608 is incorporated within the imaging scanner assembly 600, as further described herein. The reader 100 is configured to read one or more of the memory devices 308, 510, 608. In one example, the memory devices 308, 510, 608 include data stored or contained therein including, but not limited to, identification data/parameters including statistical process date, use data, parameters such as mechanical, electrical parameters and the like, calibration parameters (e.g., tip area functions, voltage—displacement and force relationships, and the like) and the like. The reader 100 reads data from one or more of the memory devices 308, 510, 608 and communicates with the controller 50 to calibrate one or more of the mechanical instrument assembly, one of the mechanical instruments (e.g., the probe tip, transducer assembly, the imaging scanner assembly and the like). Optionally, the reader 100 reads data from one or more of the memory devices 308, 510, 608 to provide identification, usage data, statistical process information and the like to the nanomechanical test system 30.

Examples of nanomechanical test systems suitable to be configured for use with embodiments of the present disclosure are described in U.S. Pat. Nos. 5,553,486 and 5,869,751, both of which are assigned to the same assignee as the present disclosure and incorporated herein by reference. For instance, test systems suitable for use with the disclosure include, but are not limited to, optical microscopes, scanning probe microscopes (SPM), electron microscopes and the like. Another test system suitable for use with the present disclosure is an electron microscopy (e.g. transmission electron (TEM) and/or scanning electron (SEM)) in-situ nanomechanical tester commercially available under the trade name PicoIndenter from Hysitron, Incorporated, of Minneapolis, Minn., USA.

Figure 2:
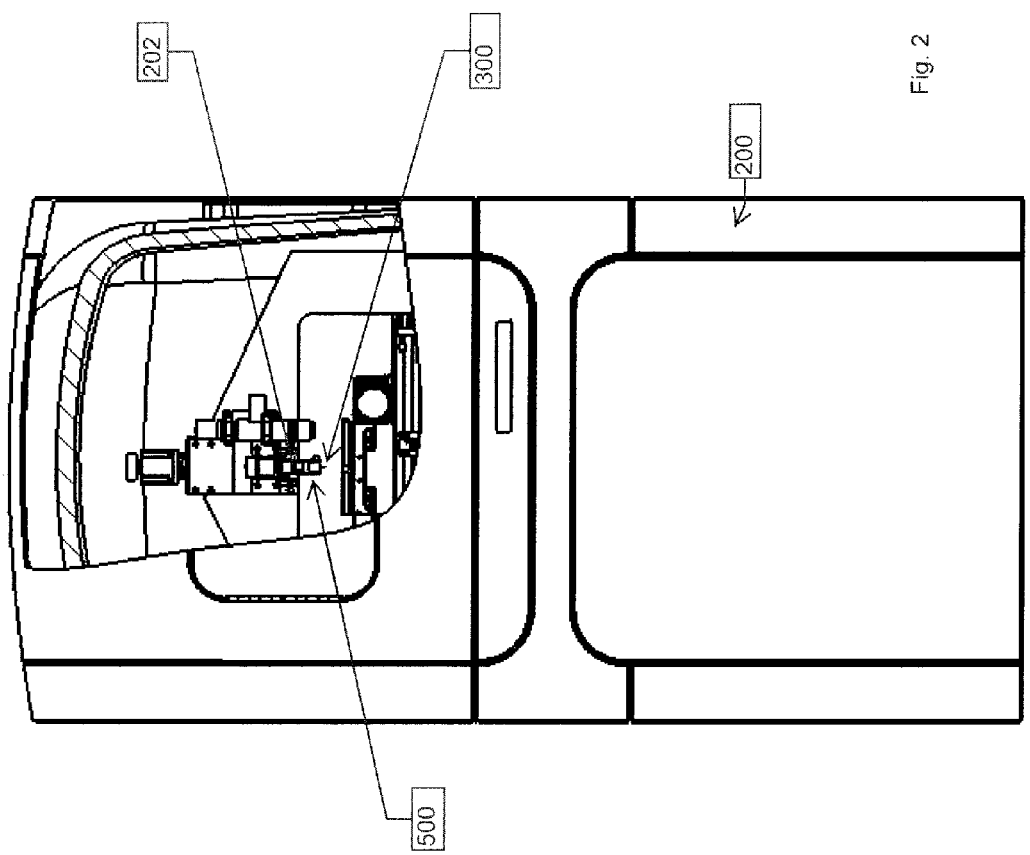
FIG. 2 is a front view showing one example of a mechanical instrument assembly configured for mechanical testing at a sub-micron scale.

FIG. 2 shows one example of a mechanical instrument assembly housing 200 including a mechanical instrument assembly 202 therein. In one example the mechanical instrument assembly housing 200 further includes a controller such as the controller 50 and the computer 40 shown in FIG. 1. The computer 40 provides an interface for operation of the controller 50 as well as the mechanical instrument assembly 202 shown in FIG. 2. For a more detailed discussion of the operation of the mechanical instrument assembly 202 reference is made to FIG. 1 and the associated specification previously described herein. The mechanical instrument assemblies described herein and usable with the system shown in FIG. 1 as well as the mechanical testing instruments described herein include, but are not limited to, Scanning Probe Microscopes, Transmission Electron Microscopes, Scanning Electron Microscopes and the like.

In one example, the computer 40 shown in FIG. 1 is used to interface with one or more mechanical testing instruments and receive calibration data for one or more of those instruments. For instance, one or more of a probe tip, a transducer assembly, an imaging scanner assembly and the like includes one or more calibration values included with the appropriate mechanical testing instrument for use by the mechanical instrument assembly 202 in calibrating the mechanical instrument assembly to accurately measure forces, displacement and the like through the use of the mechanical testing instrument. As described in further detail below, one or more of the mechanical testing instruments includes calibration values unique to the mechanical testing instrument. For instance, where the mechanical testing instrument includes a probe tip assembly the probe tip assembly includes on-board calibration values that approximate an area function based on the actual unique tip geometry of that particular probe tip. By including the calibration values with the mechanical testing instrument such as the probe tip the user is able to rapidly install and use the mechanical instrument assembly 202 and the mechanical testing instruments therein Importantly, the mechanical instrument assembly 202 is able to use unique calibration data (values) specific to the particular mechanical testing instrument to provide accurate measuring capability for forces, displacement and the like for the mechanical instrument assembly 202. Use of testing instruments including onboard calibration values eliminates the need for manual entry of calibration data from accompanying literature for instance, and thereby eliminates user error.

Figure 3:
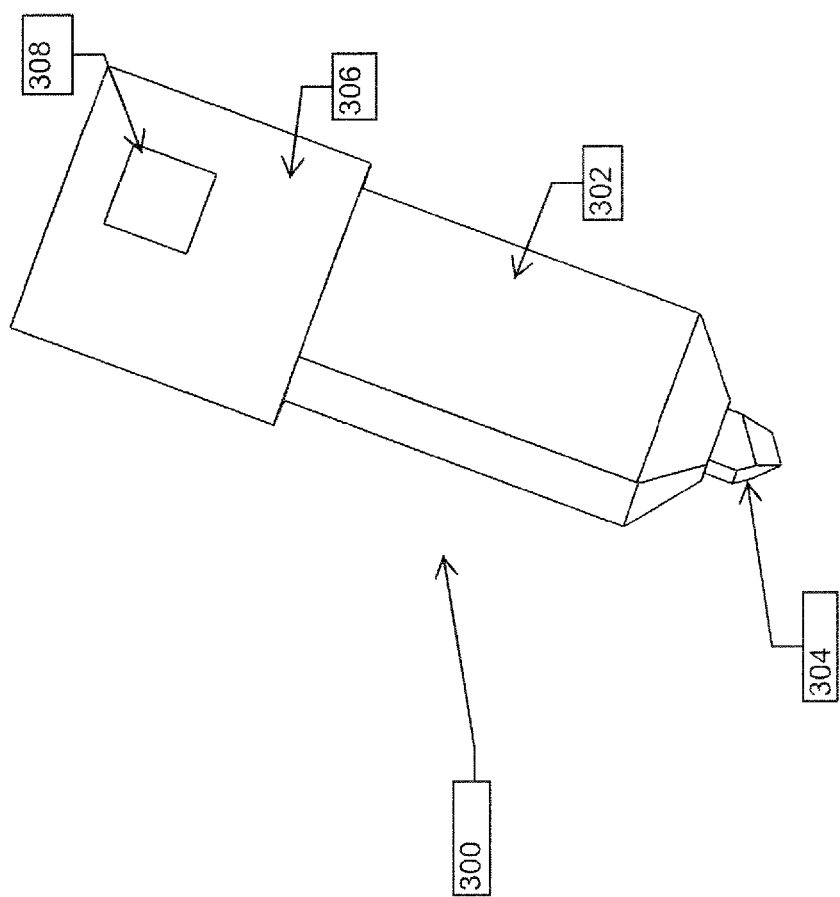
FIG. 3 is a perspective view of one example of a probe tip for use with the mechanical instrument assembly shown in FIG. 2.

FIG. 3 shows one example of a probe tip assembly 300. As shown the probe tip assembly 300 includes a probe tip 304 received within a tip holder 302. The tip holder 302 is in turn coupled with a tip holder mount 306 configured for coupling with a transducer assembly (described below). In one example the tip holder mount 306 is configured for coupling with a post and the post is in turn coupled with the transducer assembly. In another example, the probe trip is constructed with a hard material including, but not limited to, diamond and the like. One or more of the tip holder 302 and the tip holder mount 306 are constructed with materials including, but not limited to, materials having a known modulus of elasticity including for instance Zerodur® (a registered trademark of Schott AG) and Clearceram® (a registered trademark of Kabushiki Kaisha Ohara TA Ohara, Incorporated).

Referring again to FIG. 3, the probe tip assembly 300 further includes a memory device 308 coupled with the probe tip assembly. As will be described in further detail below, the memory device 308 includes one or more calibration values corresponding to values of mechanical characteristics particular to the probe tip assembly 300. For instance the memory device 308 includes calibration values for the shape of the probe tip 304, the materials of one or more of the probe tip 304, the tip holder 302 and the tip holder mount 306. In another example the memory device 308 includes a serial number configured to correspond with calibration values held in a database, for instance a database contained within the controller 50 or computer 40 shown in FIG. 1. In another example, the memory device 308 includes but is not limited to one or more of the following: a wired chip (having electrical contacts), a radio frequency identification device (RFID), a bar code, characters capable of optical character recognition, an inductance chip and the like. Optionally, the memory device includes identification parameters, including, but not limited to, statistical process data, industry standard values for the probe tip, industry thresholds for the same, serial numbers and the like. Each of these types of memory devices 308 is configured to include data as described herein.

As previously described above the memory device 308 associated with the probe tip assembly 300 includes unique calibration values based on actual mechanical characteristics of the probe tip 304, tip holder 302, tip holder mount 306 and the like. Optionally, as also described above, instead of or in addition to including the unique calibration values the probe tip assembly 300 includes a serial number corresponding to a serial number held in a database for instance within one of the controller 50 or computer 40 shown in FIG. 1. The serial number corresponds with a calibration value approximating one or more of the shape of the probe tip 304, materials of the tip holder 302 or the materials of the tip holder mount 306 respectively. In the example where the memory device 308 on the probe tip assembly 300 includes the unique calibration values based on the actual mechanical characteristics of the probe tip 304, in one example those calibration values approximate the shape of the probe tip 304 and are used to calibrate the mechanical instrument assembly 202 shown in FIG. 2 according to the unique shape of the individual probe tip 304.

In one example the calibration value of the probe tip assembly 300 includes an area function providing a polynomial equation that relates the cross sectional area of the probe tip 304 at the intersection with a sample with any depth penetration of the probe tip 304 within a specified range. In other examples, other equations or values capable of modeling the probe tip 304 are used. By providing an area function that is unique to the probe tip shape accurate and precise measurements of force, displacement penetration and the like are generated with the probe tip assembly 300 when used with the mechanical instrument assembly 202 shown in FIG. 2. Stated another way, mechanical characteristics of a sample such as an elastic modulus, hardness and the like are accurately determined where the mechanical instrument assembly 202 is calibrated according to the unique shape of the probe tip 304 using the calibration values such as the area function described herein. The memory device 308 provides a system for onboard inclusion of one or more of identification information, calibration values, statistical process information and the like unique to the mechanical testing instrument, in this example, the probe tip assembly 300. In other examples, memory devices incorporated with the transducer assembly, imaging scanner assembly and the like provide onboard one or more of identification information, calibration values, statistical process information and the like unique to the mechanical characteristics of those mechanical testing instruments.

Figure 4:
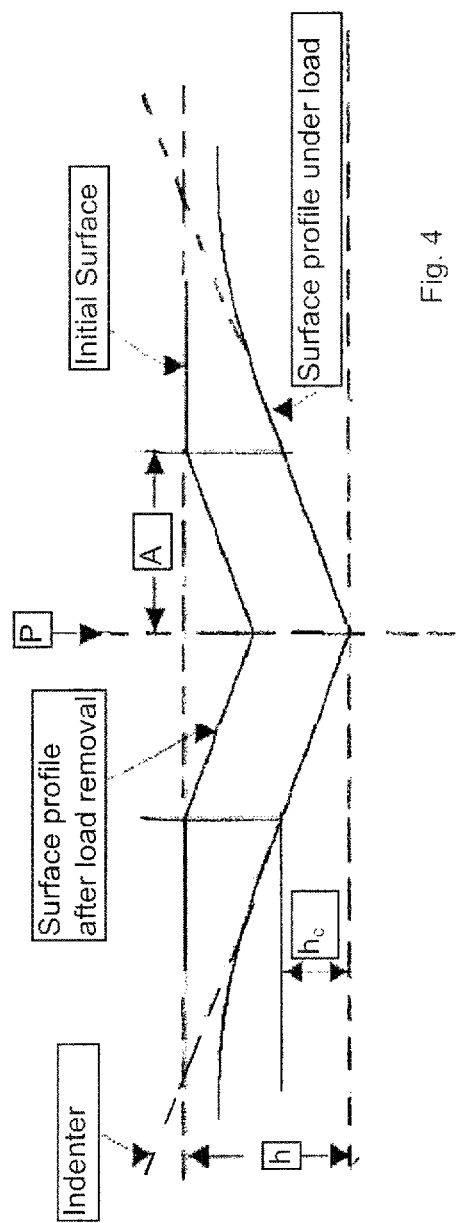
FIG. 4 is a diagram showing one example of a sample during and after indentation in relation to an area function of a probe tip.

In one prophetic example the area function is determined according to the following analysis. As shown in FIG. 4, the cross sectional area of an indentation is provided showing a surface of a sample while under load and the surface of the sample after removal of the load. One prophetic example of the determination of an area function as a calibration value for a probe tip is provided below.

Performing a probe calibration for each probe will compensate for non-perfect or unique probe shape. The initial shape of the probe tip 304, the probe radius of curvature and change in shape of the probe can be determined and redetermined in the case of dulling and use for the probe. This information is used for calibrating and recalibrating the mechanical instrument assembly 202 according to the unique probe tip 304 or probe assembly 300.

During an indentation, the indenter probe is driven into a sample and then withdrawn by decreasing the applied force. The applied load P and depth of penetration h into the sample are continuously monitored and a load versus displacement plot is produced.

The contact area is determined from the probe area function $A(h_c)$ where $h_c$, the contact depth, is found with:

$$h_c = h_{max} - \varepsilon \frac{P_{max}}{S}$$

To account for edge effects, the deflection of the surface at the contact perimeter is estimated by taking the geometric constant as 0.75. The cross-sectional area of an indentation shown in FIG. 4 illustrates the relationship of P, A, $h_c$ and h.

The reduced modulus is related to the modulus of elasticity E with:

$$\frac{1}{E_r} = \frac{1-v^2}{E_{sample}} + \frac{1-v^2}{E_{indenter}}$$

For a standard diamond indenter probe, $E_{indenter}$ is 1140 GPa and $v_{indenter}$ is 0.07. Poisson's ratio varies between 0 and 0.5 for most materials. The hardness has the normal definition given by:

$$H = \frac{P_{max}}{A}$$

Where $P_{max}$ is the maximum indentation force and A is the resultant projected contact area at that load. The reduced modulus is defined as:

$$E_r = \frac{S\sqrt{\pi}}{2\sqrt{A}}$$

Where S is the stiffness of the unloading curve and A is the projected contact area. The initial unloading contact stiffness (the slope of the initial portion of the unloading curve) is defined by:

$$S = \frac{dP}{dh}$$

Rearranging and substituting the above equations yields:

$$A = \frac{\pi}{4}\left[\frac{S}{E_r}\right]^2$$

To determine the area function, a series of indents at various contact depths (varying normal loads) are performed in a sample of known elastic modulus (typically fused quartz) and the contact area A is calculated. A plot of the calculated area as a function of contact depth is created and a software function (e.g., a TriboScan software) fits the A versus $h_c$ curve to the sixth order polynomial:

$$A = C_0 h_c^2 + C_1 h_c + C_2 h_c^{1/2} + C_3 h_c^{1/4} + C_4 h_c^{1/8} + C_5 h_c^{1/16}$$

$C_0$ for an ideal Berkovich probe is 24.5 while for a cube corner (90 degrees) probe is 2.598 with $C_1$ through $C_5$ set equal to zero. In order to fit the shape of the actual probe geometry, $C_1$ through $C_5$ will be allowed to vary.

The Area Function described herein provides one example of a function that provides a relation between indentation depth and the area of the probe tip 304 according to the unique shape of the probe tip 304. By using a series of indentations with varying depths (loads) and knowledge of the known sample modulus of elasticity, areas for each indentation are determined and the area function is fit to the area measurements. The area function is a calibration value unique to the probe tip 304 and stored in the memory device 308 of the probe tip assembly 300 (e.g., as the calibration value in a memory, characters in a bar cord or optical character recognition formatted text and the like). The calibration value is used to calibrate the mechanical instrument assembly 202 and ensures accurate measurements of force, displacement and the like for mechanical testing.

Including the memory device 308 with the mechanical testing instrument such as the probe tip assembly 300 shown in FIG. 3 consolidates the calibration values with the probe tip assembly and thereby eliminates the need for separate literature, software (compact discs, on-line downloading and the like). Instead, the calibration values for the particular mechanical characteristics of the unique probe tip assembly 300 are incorporated with the probe tip assembly having that unique corresponding shape. By incorporating the memory device 308 with the probe tip assembly 300 operator confusion and error is eliminated between other systems using literature and a separate tip.

Further, by incorporating a memory device 308 with a probe tip assembly 300 a ready medium is provided to readily update the calibration values as described herein and ensure consistent and accurate displacement and force measurements are taken with the probe tip assembly 300 over the lifetime of the probe tip 304. In one example, prior to use of the probe tip assembly 300 with samples requiring examination the probe tip assembly is calibrated by indenting the probe tip 304 repeatedly within a sample having known material characteristics such as quartz, aluminium and the like. The probe tip 304 is indented into the material multiple times under various forces and with various displacements. The calibration values such as an area function are determined from these initial indentations. Calibration values including the area function based on these initial indentations are scanned into the memory device 308, in one example. In another example, the memory device 308 incorporates a serial number corresponding to the calibration values within a database such as a database held in computer 40 or controller 50 shown in FIG. 1.

After the probe tip assembly 300 is used for mechanical testing purposes, for instance after 100, 200, 500 or 1,000 indentations and the like, the probe tip 304 will necessarily experience at least some wear and thereafter not have the same original shape as when used for the initial indentations. The mechanical instrument assembly 202 is configured to recalibrate for the probe tip assembly 300 with the altered probe tip shape by conducting supplemental indentations for calibration purposes with a known sample such as quartz, aluminum and the like. In one example a mechanical instrument assembly 202 re-performs (or performs for the first time in the case of a probe tip 304 with initial calibration values) the indentations and develops an updated calibration value such as an area function and writes the calibration value into the memory device 308 of the probe tip assembly 300. In this way the calibration values of the probe tip assembly 300 are updated over the working lifetime of the probe tip assembly 300 to ensure consistent and accurate displacement and force measurements over the probe tip lifetime. Optionally, the calibration values including preceding and dated calibration values are stored in the memory device 308 (or controller 50 or computer 40) for later analysis.

In another example, after redetermination of the calibration values if the tip is unable to meet bare threshold values (e.g. for shape, area function and the like) whether initially or during re-calibration of the probe tip assembly 300 the user is informed that re-calibration is not possible and the memory device 308 is written with corresponding information. The probe tip assembly 300 can no longer be used (i.e., it is not recognized by the mechanical instrument assembly 202, is locked out and the like). By providing base threshold values for instance with the mechanical instrument assembly 202 or memory devices of the mechanical testing instruments inherent quality control is provided with the mechanical instrument assembly 202 to prevent the use of substandard probe tip assemblies or probe tip assemblies that are no longer capable (after repeated use, through faulty manufacturing or damage) of providing accurate displacement and force measurements based on the inability of the probe tip 304 to meet threshold calibration or parameter values.

In another example, the memory device 308 incorporated with the probe tip assembly 300 is configured to provide statistical process control information to ensure the probe tip assembly 300 meets industry standards (e.g., identification characteristics/parameters such as ISO standards, such as ISO standard 14577 for nano-indentation). For instance, the memory device 308 in one example includes a certification that the probe tip assembly 300 as provided has an ISO standard tip shape calibration value, calibration method and the like. The memory device 308 thereby identifies the probe tip assembly 300 as a standardized probe tip assembly (ISO standardized) and permits the use of the probe tip assembly within the mechanical instrument assembly 202. In another example, the standardized information provided on the memory device 308 provides basic threshold values for the calibration values used with the probe tip assembly. Stated another way, the memory device 308 includes not only the calibration values for the probe tip assembly 300 but also the basic threshold values dictated by industry standards such as ISO standards for the probe tip assembly. As the probe tip assembly 300 is used the probe tip 304 is subject to wear as described above. The memory device 308 thereby provides the basic thresholds used to compare the performance of the probe tip 304 after use. These values (the basic threshold values and updated calibration values) are compared for instance by the mechanical instrument assembly 202 to determine whether the probe tip assembly 300 is capable of continued use within the mechanical instrument assembly 202. Provision of the standardized calibration values (minimum calibration values) thereby provides a confidence measure that the probe tip assembly 300 satisfies the relevant industry standards such as ISO standards. Optionally, the threshold values are stored within one or more of the controller 50 and computer 40 of the mechanical instrument assembly 202.

In another example, providing a memory device 308 in the probe tip assembly 300 facilitates the identification of probe tips used in mechanical instrument assemblies for quality control. In some examples probe tips will not have the right shape or will be constructed with varying materials that prevent or frustrate the ability to accurately measure displacement and forces over the lifetime of the probe tip 304. By including identification parameter information such as the probe tip shape, materials, serial numbers, ISO standards and the like with the probe tip assembly memory device 308 the mechanical instrument assembly 202 is able to scan for this information and prevent the use of probe tip assemblies that fail to include specified materials, tip shapes and the like. A mechanical instrument assembly 202 when used with the probe tip assembly 300 is thereby able to prevent the use of substandard or varying probe tip assemblies and thereby ensures the accurate measurement of forces in displacement with conforming probe tips having the appropriate materials, tip shapes and the like.

Figure 5B:
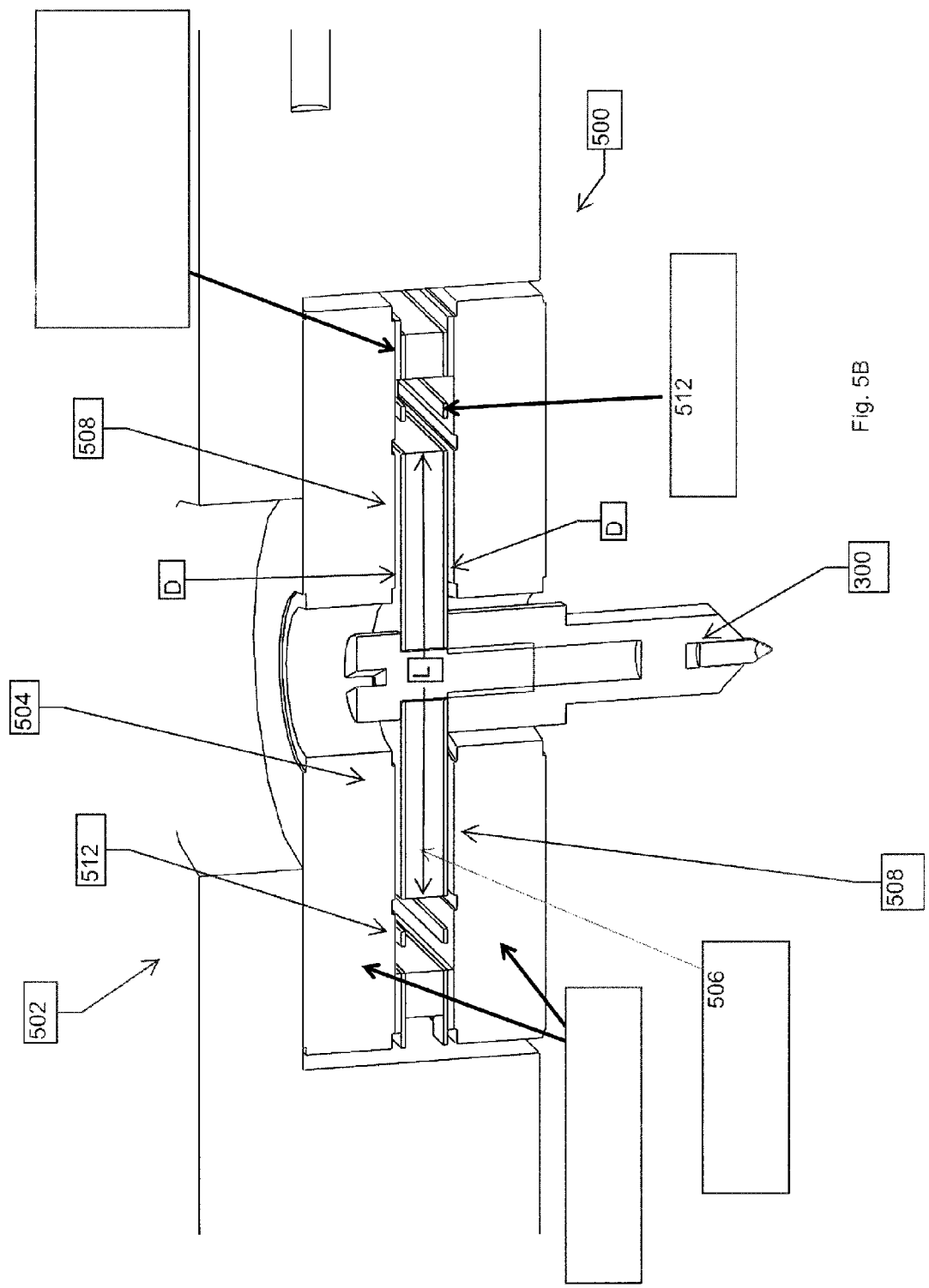
FIG. 5B is a detailed perspective and cross sectional view of the transducer assembly shown in FIG. 5A.

FIGS. 5A, B show one example of a mechanical testing instrument including a transducer assembly 500. The transducer assembly 500 includes a transducer housing 502 sized and shaped to house a transducer 504 therein. In the example shown in FIGS. 5A, B, one example of a transducer 504 is provided including a center plate 506 and counter electrodes 508. The center plate 506 and counter electrodes 508 of a capacitive transducer 504 operatively coupled with a probe tip assembly such as the probe tip assembly 300 shown in FIG. 3. For instance, the center plate 506 is coupled with the probe tip assembly 300 and electrostatic actuation of the transducer 504 through voltage applied to the counter electrodes 508 actuates the center plate 506 and thereby correspondingly actuates the probe tip assembly 300. In a similar manner, movement of the probe tip assembly 300 is measurable through voltage changes across the counter electrodes 508 to measure the displacement of the probe tip assembly as well as force applied to the probe tip assembly for instance through engagement with a sample.

As shown in FIGS. 5A, B, the transducer assembly 500 includes a memory device 510. As previously described for the probe tip assembly 300, the memory device 510 for the transducer assembly 500 includes one or more calibration values based on unique mechanical characteristic values of the transducer assembly 500 (and optionally identification parameters and the like). For instance, in one example the memory device includes calibration values corresponding to the spring constant for springs 512 that couple the center plate 506 with the transducer housing 502 in the transducer 504. In another example, the calibration values include one or more of relations between voltage applied and force provided to the probe tip assembly 300 by the transducer 504 and displacement of the probe tip assembly relative to voltage measured across the counter electrodes 508. Optionally, the memory device includes one or more serial numbers corresponding to calibration values found in a database such as the computer 40 or the controller 50 shown in FIG. 1. The calibration values included in the memory device are provided to facilitate the calculation of hardness, modulus, sample forces, displacement and the like using the transducer assembly 500 with the probe tip assembly 300 installed within the mechanical instrument assembly 202 shown in FIG. 2. As with the memory device 308, the memory device 510 for the transducer assembly 500 includes in other examples (in addition to or alternatively) identification data/parameters, statistical process information, industry standard instrument data for the transducer (such as its material, spring constant and the like) as well as industry standard thresholds that must be met for use with the mechanical instrument assembly 202.

As previously described, provision of the memory device 510 on the transducer assembly 500 consolidates the calibration values with the transducer assembly and matches the unique calibration values with the transducer assembly 500 having a corresponding mechanical structure with mechanical characteristics corresponding to those calibration values. Stated another way, the calibration values stored in the memory device correspond to values of mechanical characteristics such as spring constants, capacitor plate areas (e.g., based on radius, diameter, length l, width w and the like of the plates) and separation distances (e.g., d) between capacitor plates such as the counter electrodes 508 and the center plate 506 of the transducer 504 and the like. Minor inconsistencies such as manufacturing and material inconsistencies and the like are thereby accounted for in the memory device 510 through use of the calibration values. Accurate and precise measurements of forces, displacements, voltages and the like are thereby automatically attained and realized through the use of the unique calibration values stored within the memory device corresponding to the unique mechanical structure of the particular transducer assembly 500 read by the mechanical instrument assembly 202.

In the example of a calibration value including a spring constant the transducer assembly 500 in one option is operated through a series of air indents where the transducer assembly receives a voltage applied across the counter electrodes 508 to actuate the center plate 506 while no sample is otherwise present or engaged with the probe tip assembly 300. The voltage actuates the transducer 504 and generates a force and displacement of the transducer 504. The electrostatic force or the displacement are used to determine the spring constant. This relationship between the voltage and one or more of force and displacement is used to form a calibration value written to the memory device for use with the transducer assembly 500.

In one example, the mechanical instrument assembly 202 reads the data from the memory device and applies the appropriate calibration value to calculations used to determine force displacement and the like using the transducer assembly 500 installed therein. Optionally, the series of air indents, other testing procedures and the like are performed after a set number of indentations or operations of the transducers or when performance of the transducer assembly 500 is suspected to have significantly changed (e.g., after 100, 500, 1000 operations or when a skewed test result is observed). By repeating the testing scheme, such as the air indents, calibration values are reevaluated. In one example, the calibration values are written to the memory device 510 and stored with the transducer assembly 500 therein. The mechanical instrument assembly 202 is thereafter able to read the updated calibration values from the memory device and adjust measurements received from the transducer assembly 500 accordingly to compensate for changes in one or more of the spring constant or relations between voltage and force or displacement and voltage.

Further, in a similar manner to the probe tip assembly 300 the memory device of the transducer assembly 500 includes, in one option, threshold calibration values or threshold mechanical characteristic values. In one example these threshold values are compared with the updated calibration values of the transducer assembly 500 or updated mechanical characteristic values of the transducer assembly 500 to determine whether or not the transducer assembly 500 meets minimum requirements for operation (e.g. accurate measurement of force displacement and the like). In still another example, the transducer assembly memory device 510 includes minimum standardized values such as ISO standardized values for use in comparison with the calibration values of the transducer assembly 500. As described previously, provision of standardized values such as ISO standardized values provides a confidence measure to the transducer assembly 500 that assures a user that the transducer assembly will under all circumstances operate at least to ISO standards and after failure of the transducer assembly 500 to meet such standards, for instance where the calibration values dip below the standardized threshold values, the mechanical instrument assembly 202 will no longer recognize the transducer assembly 500 and thereby prevent its use for mechanical testing measurements.

In the case of both the probe tip assembly 300 and the transducer assembly 500, in one example the mechanical instrument assembly 202 or a remote tracking system tracks items such as the number of indents on a probe tip 304, a change (or changes) in the transducer assembly tip area function, other mechanical value changes such as spring constant changes and the like. One example of this data is stored within the memory devices 308, 510 at the respective transducer assembly 500 and probe tip assembly 300. Optionally this information is tracked within the mechanical instrument assembly 202, for instance in the memory 84. In still another example this data is transmitted through an information link such as an Ethernet or wireless link across the internet to a remote analysis system. By tracking this data and incorporating software analysis within one or more of the mechanical instrument assembly 202 or a remote system analysis is possible to determine wear rates for various test conditions and whether the probe tip 304, transducer assembly 500 or the like has been damaged, broken or is worn out. In another option warranties may be offered based on the analysis gained using such tracking data such as the number of indents, wear rate and the like.

Figure 6:
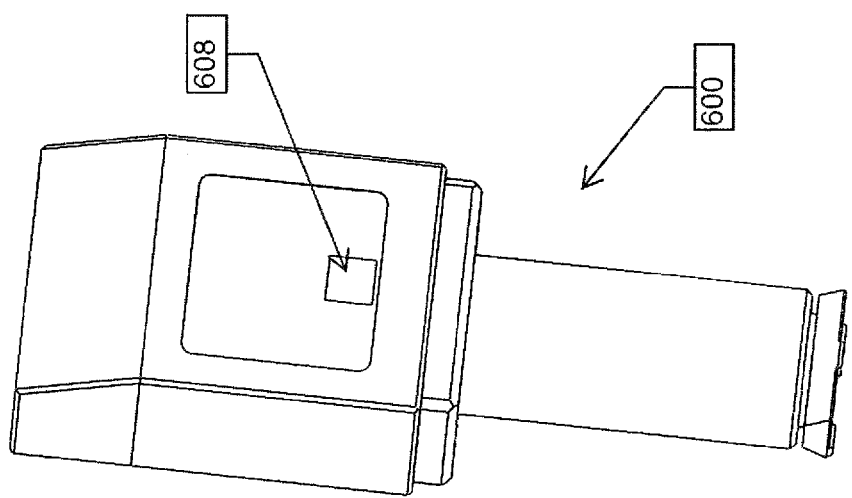
FIG. 6 is a perspective view of one example of an imaging scanner assembly for use with the mechanical instrument assembly shown in FIG. 2.

FIG. 6 shows one example of an imaging scanner assembly 600 configured to create images from sample surfaces. In a similar manner to the transducer assembly 500 the imaging scanner assembly 600 includes a transducer 504 such as capacitive transducer coupled with a tip. The tip is, in one example, scribed over a surface such as a surface of a sample and movement of the tip along a Z axis coincident with the axis of the probe tip 304 is used to scan and map the surface of the sample. Additionally, the tip is capable of moving laterally according to actuation through actuation voltages applied across the transducer 504. The tip is thereby able to move in the X and Y plane for instance scribing the tip across the surface of the sample.

As shown in FIG. 6, the imaging scanner assembly 600, similarly to the probe tip assembly 300 and the transducer assembly 500, is a mechanical testing instrument including a memory device 608. As with the previous examples, the memory device 608 of the imaging scanner assembly 600 is configured to store one or more calibration values (and optionally identification parameters and the like) used in operation of the imaging scanner assembly 600 to ensure accurate measurements of, for instance, displacement in the X, Y and Z plains. In one example the memory device 608 includes one or more serial numbers corresponding to calibration values stored in the computer 40 or controller 50 as shown in FIG. 1. The mechanical instrument assembly 202 shown in FIG. 2 uses the calibration values for operation of the mechanical instrument assembly to ensure scanning accuracy of the imaging scanner assembly 600. In still another example, the memory device 608 includes calibration values corresponding to unique mechanical characteristic values of the imaging scanner assembly 600 such as the spring constant of the transducer 504 (e.g., the springs 512 supporting the center plate 506 of the transducer 504) or a relation displacement relative to voltage changes across the transducer 504 and the X and Y plains and displacement relative to voltage changes across the transducer 504 for actuation in the Z or normal plain.

Additionally, and in the case of each of the mechanical testing instruments such as the imaging scanner assembly 600, the transducer assembly 500 and the probe tip assembly 300 the memory device 308, 510, 608 further includes tracking serial numbers and the like to ascertain the manufacturing characteristics of the mechanical testing instruments such as the date of manufacture, where they were manufactured, which batch they were manufactured with and the like. In still other examples, each of the memory devices 308, 510, 608 described herein includes one or more of a passkey that unlocks functionality of the mechanical testing instrument, mechanical instrument assembly 202 and the like for testing schemes. Such testing schemes include, but are not limited to, medical device testing schemes, testing schemes for particular materials, proprietary testing schemes and the like. Optionally, the memory devices 308, 510, 608 include other information including, but not limited to, use data such as number of indents with the mechanical testing instrument, scratches and the like; instructions for specified testing schemes, protocols and the like for use by the user or the mechanical instrument assembly 202. As with the memory devices 308, 510, the memory device includes in other examples (in addition to or alternatively) identification data/ parameters, statistical process information, industry standard instrument data for the transducer (such as its material, spring constant and the like) as well as industry standard thresholds that must be met for use with the mechanical instrument assembly 202.

Further, in another example, the tracking serial number indicates the material used in the mechanical testing instrument, the structural configuration of the mechanical testing instrument and the like. In one example the memory device 308, 510, 608 facilitates the storage of a set of sequential calibrations that define one or more run charts or control charts of one or more variables to allow the instrument user or original equipment manufacturer to verify if the transducer performance has changed with time (e.g., transducer 504 of the transducer assembly 500 or a transducer used within the imaging scanner assembly 600). This is the case with either of the imaging scanner assembly 600, the probe tip assembly 300 or the transducer assembly 500. Additionally, by providing calibration values on a memory device 308, 510, 608 capable of being rewritten or updated and cataloged the mechanical instrument assembly 202 is capable of performing updated calibration tests on the imaging scanner assembly 600. For instance, calibration testing is performed after 100, 200, 1,000 or more indentations to measure the relation of displacement to voltage applied to the transducer 504 and thereafter update the calibration values for use in operation of the imaging scanner assembly 600 to assure accurate measurement of displacement. In still another example, updated calibration values are held within the memory of the mechanical instrument assembly 202 such as the controller 50 or memory 84 for the computer 40. As with previous examples, the imaging scanner assembly memory device 608 includes, in one example, standardized threshold values providing for the calibration values and substantially preventing the use of the imaging scanner assembly 600 where the updated calibration values fail to meet the minimum standardized value scan therein.

As discussed herein, the memory device 308, 510, 608 for any of the mechanical testing instruments (e.g., the probe tip assembly 300, the transducer assembly 500 and the imaging scanner assembly 600) store a variety of data for use in the operation of the mechanical instrument assembly 202 (e.g., calibration, determination of minimum standardized requirements and the like). Additionally data is stored on the memory devices 308, 510, 608 for analysis (wear, use and the like) and passkey functionality purposes (e.g., to unlock additional testing schemes, protocols and the like). In still other options, data is stored on the memory devices 308, 510, 608 for tracking purposes, material and shape identification and the like.

Figure 7:
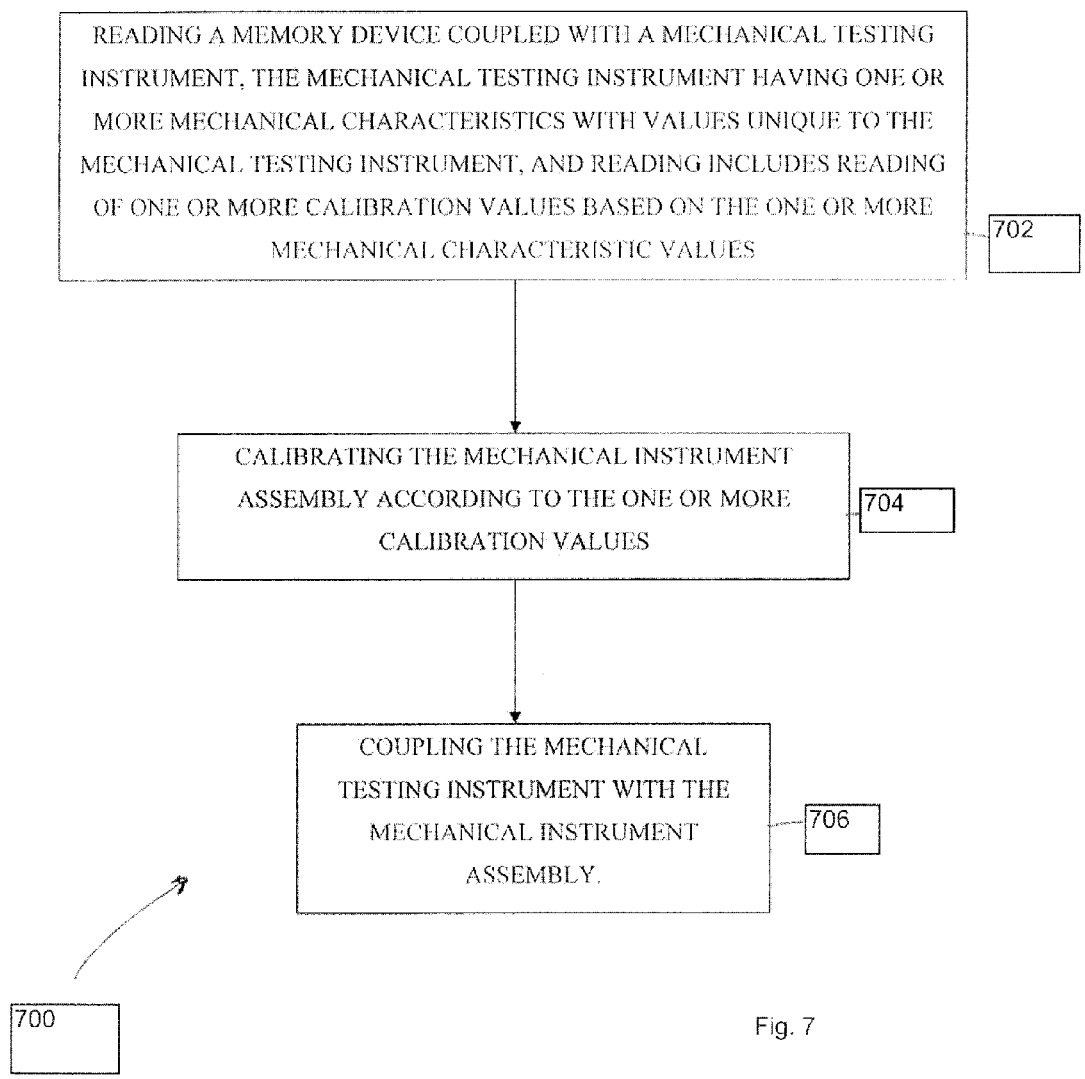
FIG. 7 is a block diagram showing one example of a method for calibrating a mechanical instrument assembly.

FIG. 7 shows one example of a method 700 for calibrating a mechanical instrument assembly such as the mechanical instrument assembly 202 shown in FIG. 2. Reference is made in the description of the method 700 to one or more elements previously described in the specification. Where reference is made to a numbered element previously described herein the reference is not intended to be limiting and instead should include other corresponding features found in other examples as well as their equivalents.

Referring to FIG. 7, at 702 the method 700 includes reading a memory device coupled with a mechanical testing instrument (e.g. a memory device 308, 510, 608 coupled with one or more of a probe tip assembly 300, a transducer assembly 500 or an imaging scanner assembly 600). The mechanical testing instrument has one or more mechanical characteristics with values unique to the mechanical testing instrument such as but not limited to spring constant, tip shape, voltage relationships to force and displacement and the like. Reading the memory device 308, 510, 608 includes reading one or more calibration values (e.g., calibration data including area functions, shapes, materials and the like, identification data, statistical process data and information, operational thresholds and the like) based on the one or more mechanical characteristic values. As previously described the one or more calibration values are unique calibration values corresponding to the unique mechanical characteristic values of each of the mechanical testing instruments including the memory device 308, 510, 608.

At 704, the method 700 further includes calibrating the mechanical instrument assembly 202 according to the one or more calibration values. For instance, the memory devices 308, 510, 608 coupled with one or more of the probe tip assembly 300, the transducer assembly 500 and the imaging scanner assembly 600 are read through a reader or scanner (e.g., reader 100 of the nanomechanical test system 30 in FIG. 1) on the mechanical instrument assembly 202 to upload the calibration values for operation of the mechanical instrument assembly. Optionally, the memory devices 308, 510, 608 include serial numbers corresponding to calibration values held within a database in one or more of the computer 40, controller 50 or memory 84 shown in FIG. 1.

At 706, the method 700 includes coupling the mechanical testing instrument with the mechanical instrument assembly 202. For instance, one or more of the imaging scanner assembly 600, transducer assembly 500 and probe tip assembly 300 are installed within the mechanical instrument assembly 202 for use of the assembly in measuring one or more of displacement for supply to a sample force transmitted to a probe tip 304 and the like. Optionally, reading the memory devices 308, 510, 608 is conducted contemporaneously to coupling of the mechanical testing instrument with the mechanical instrument assembly 202 or prior to operation of the mechanical instrument assembly.

Several options for the method 700 follow. In one example the method 700 further includes performing analysis of the mechanical testing instrument to update the values of the one or more mechanical characteristics or calibration values based on the mechanical characteristics (e.g. tip shape spring constant voltage displacement relations voltage to force relations and the like). In another example the method further includes writing over or writing additional data to the memory device 308, 510, 608 including updated calibration values based on the updated values of the one or more mechanical characteristics.

In another example, reading the memory device 702 includes reading the memory device 308, 510, 608 with the mechanical instrument assembly 202 for instance with a scanner 100 integrated with a mechanical instrument assembly 202. In another example the memory device 308, 510, 608 is read with a reader associated with a separate computer terminal remote from the mechanical instrument assembly 202.

The method 700 includes in another example reading the memory device 308 where the memory device 308 is coupled with mechanical testing instrument, such as a probe tip assembly 300, and the one or more mechanical characteristics includes a tip shape of the probe tip 304. In still another example, coupling the mechanical testing instrument with the mechanical instrument assembly 202 includes coupling the probe tip assembly 300 with a transducer assembly 500. In one example a post, rod or the like is coupled between the probe tip assembly 300 and the transducer assembly 500 thereby positioning the probe tip 304 some distance remotely from the transducer assembly 500. In another option, calibrating the mechanical instrument assembly 202 according to the one or more calibration values as previously described above includes calibrating the mechanical instrument assembly 202 with an area function based on the tip shape wherein the area function relates an indentation depth with a cross sectional area of the probe tip 304. As previously described, the area function relates an indentation depth with a unique cross sectional area of the probe tip 304.

The method further includes in another example, reading the memory device 510 coupled with the mechanical testing instrument such as a transducer assembly 500 and the one or more mechanical characteristics includes a spring constant of a deflectable support element coupled between the transducer 504 and a transducer body. For instance, the deflectable support element includes a spring 512 coupled between the center plate 506 of a transducer 504 and the transducer housing 502. Optionally, the method 700 includes coupling of the transducer assembly 500 with the mechanical instrument assembly 202. In still another option, calibrating the mechanical instrument assembly 202 includes calibrating the mechanical instrument assembly 202 with the spring constant of the deflectable support element (e.g., the spring 512) within the transducer assembly 500.

In still another example, reading the memory device coupled with mechanical testing instrument includes reading a memory device 510 coupled with a transducer assembly 500, and the one or more mechanical characteristics includes at least one of a transducer capacitor plate area and separation between plates of a transducer 504. In the same example calibrating the mechanical instrument assembly 202 according to the one or more calibration values includes calibrating the mechanical instrument assembly 202 with a relation between voltage applied to the transducer 504 and force supplied by the transducer 504 based on one or more transducer capacitor plate area and separation between plates and the transducer 504. In still another example, calibrating the mechanical instrument assembly 202 includes calibrating the mechanical instrument assembly with a relation between displacement of the transducer 504 and voltage change at the transducer 504 based on one or more of transducer capacitor plate area and separation between plates of the transducer assembly 500.

In yet another example, reading the memory device coupled with the mechanical testing instrument includes reading a memory device 608 coupled with an imaging scanner assembly, such as the scanner assembly 600 shown in FIG. 6. The one or more mechanical characteristics of the imaging scanner assembly 600 include at least one of transducer capacitor plate area and separation between capacitor plates of a transducer within the scanner assembly 600 (e.g., similar to the transducer 504 of the transducer assembly 500). In one example, calibrating the mechanical instrument assembly 202 according to the one or more calibration values includes calibrating the mechanical instrument assembly with a relation between X-Y lateral displacement of the transducer 504 (where the scanner assembly 600 includes a similar transducer) and voltage change at the transducer based on one or more of transducer capacitor plate area and separation between capacitor plates of the transducer 504. In still another example, calibrating the mechanical instrument assembly 202 according to the one or more calibration values includes calibrating the instrument assembly with a relation between Z displacement of the transducer 504 and voltage change at the transducer 504 based on one or more of transducer capacitor plate area and separation between plates of the transducer.

In one option the method 700 further includes comparing the one or more calibration values with one or more threshold values (e.g., thresholds where the one or more threshold values are stored in the memory device 308, 510, 608 coupled with mechanical testing instrument or the memory 84 of the nanomechanical test system 30), for instance with a controller 50 or computer 40 associated with the mechanical instrument assembly 202. Method 700 further includes in one example determining the mechanical testing instrument is not suitable for use with the mechanical instrument assembly 202 based on the comparison with the one or more threshold values. For instance, where the calibration values of one or more of the mechanical testing instruments is updated over time according to changes in the mechanical characteristics of the instruments the calibration values are compared with the threshold values to determine whether or not the mechanical testing instrument is suitable for continued use within the mechanical instrument assembly 202. Where the calibration values fall below the minimum threshold values the mechanical instrument assembly 202 in one example fails to recognize the mechanical testing instrument and no longer allows for continued operation of the mechanical testing instrument within the mechanical instrument assembly 202. Optionally, the failure to recognize or use the mechanical testing instrument is written to the memory device 308, 510, 608 thereby precluding future use of the mechanical testing instrument. In yet another example, the method includes reading an identification parameter (e.g., serial number, industry standard identification or threshold, passkey and the like) from the memory device 308, 510, 608 coupled with the mechanical testing instrument and comparing the identification parameter with an identification threshold. Operation of a system including the mechanical testing instrument is precluded if the identification parameter does not meet the identification threshold.

EXAMPLES

Example 1 includes subject matter comprising a mechanical testing instrument having one or more mechanical characteristics with values unique to the mechanical testing instrument, and a memory device coupled with the mechanical testing instrument, and the memory device includes one or more calibration values based on the one or more mechanical characteristic values that are unique to the mechanical testing instrument.

In Example 2, the subject matter of Example 1 can optionally include the mechanical testing instrument including one or more of a probe tip, a transducer assembly and an imaging scanner assembly.

In Example 3, the subject matter of one or any combination of Examples 1-2 can optionally include wherein the one or more mechanical characteristics includes a tip shape of a probe tip.

In Example 4, the subject matter of one or any combination of Examples 1-3 can optionally include wherein the one or more calibration values includes an area function based on the tip shape.

In Example 5, the subject matter of one or any combination of Examples 1-4 can optionally include wherein the area function relates an indentation depth with a cross sectional area of the probe tip.

In Example 6, the subject matter of one or any combination of Examples 1-5 can optionally include wherein the mechanical testing instrument includes a transducer assembly and the one or more mechanical characteristics includes a spring constant of a deflectable support element coupled between a transducer and a transducer body.

In Example 7, the subject matter of one or any combination of Examples 1-6 can optionally include wherein the one or more calibration values includes the spring constant.

In Example 8, the subject matter of one or any combination of Examples 1-7 can optionally include wherein the mechanical testing instrument includes a transducer and the one or more mechanical characteristics include at least one of transducer capacitor plate area and separation between plates.

In Example 9, the subject matter of one or any combination of Examples 1-8 can optionally include wherein the one or more calibration values includes the relation between voltage applied to the transducer and force applied by the transducer.

In Example 10, the subject matter of one or any combination of Examples 1-9 can optionally include wherein the one or more calibration values includes the relation between displacement of the transducer and voltage change at the transducer.

In Example 11, the subject matter of one or any combination of Examples 1-10 can optionally include wherein the mechanical testing instrument includes an imaging scanner assembly including a transducer and the one or more mechanical characteristics include at least one of transducer capacitor plate area and separation between plates of the transducer.

In Example 12, the subject matter of one or any combination of Examples 1-11 can optionally include wherein the one or more calibration values includes the relation between x-y lateral displacement of the transducer and voltage change at the transducer.

In Example 13, the subject matter of one or any combination of Examples 1-12 can optionally include wherein the one or more calibration values includes the relation between z displacement of the transducer and voltage change at the transducer.

In Example 14, the subject matter of one or any combination of Examples 1-13 can optionally include a mechanical instrument assembly, and the mechanical testing instrument is coupled with the mechanical instrument assembly, and wherein the mechanical instrument assembly is configured to read the one or more calibration values and the mechanical instrument assembly is configured for calibration according to the one or more calibration values for sub-micron scale mechanical testing.

In Example 15, the subject matter of one or any combination of Examples 1-14 can optionally include wherein the memory device consists essentially of one or more of a radio frequency identification chip, a wired memory chip, an inductive memory chip, a bar code, visual characters capable of optical character recognition.

Example 16 can include, or can optionally be combined with one or any combination of Examples 1-15 to include subject matter such as a method, a means for performing acts, or a machine readable medium including instructions that, when performed by the machine, cause the machine to perform acts comprising reading a memory device coupled with a mechanical testing instrument, the mechanical testing instrument having one or more mechanical characteristics with values unique to the mechanical testing instrument, and reading includes reading of one or more calibration values based on the one or more mechanical characteristic values; calibrating the mechanical instrument assembly according to the one or more calibration values; and coupling the mechanical testing instrument with the mechanical instrument assembly.

In Example 17, the subject matter of one or any combination of Examples 1-16 can optionally include performing analysis of the mechanical testing instrument to update the values of the one or more mechanical characteristics; and writing over or appending the one or more calibration values with updated calibration values based on the updated values of the one or more mechanical characteristics.

In Example 18, the subject matter of one or any combination of Examples 1-7 can optionally include comparing the updated calibration values with one or more threshold values; determining the mechanical testing instrument is not suitable for use with the mechanical instrument assembly based on the comparison of the updated calibration values with the one or more threshold values.

In Example 19, the subject matter of one or any combination of Examples 1-18 can optionally include wherein reading the memory device includes reading the memory device with the mechanical instrument assembly, wherein the mechanical instrument assembly is configured to couple with the mechanical testing instrument and operate the mechanical testing instrument.

In Example 20, the subject matter of one or any combination of Examples 1-19 can optionally include wherein reading the memory device coupled with the mechanical testing instrument includes reading the memory device coupled with a probe tip, and the one or more mechanical characteristics includes a tip shape of the probe tip.

In Example 21, the subject matter of one or any combination of Examples 1-20 can optionally include wherein coupling the mechanical testing instrument with the mechanical instrument assembly includes coupling the probe tip with a transducer assembly.

In Example 22, the subject matter of one or any combination of Examples 1-21 can optionally include wherein calibrating the mechanical instrument assembly according to the one or more calibration values includes calibrating the mechanical instrument assembly according to an area function based on a tip shape, wherein the area function relates an indentation depth with a cross sectional area of a probe tip included with the mechanical testing instrument.

In Example 23, the subject matter of one or any combination of Examples 1-22 can optionally include wherein reading the memory device coupled with the mechanical testing instrument includes reading the memory device coupled with a transducer assembly, and the one or more mechanical characteristics includes a spring constant of a deflectable support element coupled between the transducer and a transducer body.

In Example 24, the subject matter of one or any combination of Examples 1-23 can optionally include wherein coupling the mechanical testing instrument with the mechanical instrument assembly includes coupling the transducer assembly with the mechanical instrument assembly.

In Example 25, the subject matter of one or any combination of Examples 1-24 can optionally include wherein calibrating the mechanical instrument assembly according to the one or more calibration values includes calibrating the mechanical instrument assembly with the spring constant of the deflectable support element.

In Example 26, the subject matter of one or any combination of Examples 1-25 can optionally include wherein reading the memory device coupled with the mechanical testing instrument includes reading the memory device coupled with a transducer assembly, and the one or more mechanical characteristics includes at least one of transducer capacitor plate area and separation between plates of a transducer.

In Example 27, the subject matter of one or any combination of Examples 1-26 can optionally include wherein calibrating the mechanical instrument assembly according to the one or more calibration values includes calibrating the mechanical instrument assembly with a relation between voltage applied to the transducer and force applied by the transducer based on one or more of transducer capacitor plate area and separation between plates of the transducer.

In Example 28, the subject matter of one or any combination of Examples 1-27 can optionally include wherein calibrating the mechanical instrument assembly according to the one or more calibration values includes calibrating the mechanical instrument assembly with a relation between displacement of the transducer and voltage change at the transducer based on one or more of transducer capacitor plate area and separation between plates of the transducer.

In Example 29, the subject matter of one or any combination of Examples 1-28 can optionally include wherein reading the memory device coupled with the mechanical testing instrument includes reading the memory device coupled with an imaging scanner assembly, and the one or more mechanical characteristic includes at least one of transducer capacitor plate area and separation between capacitor plates of a transducer.

In Example 30, the subject matter of one or any combination of Examples 1-29 can optionally include wherein calibrating the mechanical instrument assembly according to the one or more calibration values includes calibrating the mechanical instrument assembly with a relation between x-y lateral displacement of the transducer and voltage change at the transducer based on one or more of transducer capacitor plate area and separation between capacitor plates of the transducer.

In Example 31, the subject matter of one or any combination of Examples 1-30 can optionally include wherein calibrating the mechanical instrument assembly according to the one or more calibration values includes calibrating the mechanical instrument assembly with a relation between z displacement of the transducer and voltage change at the transducer based on one or more of transducer capacitor plate area and separation between plates of the transducer.

In Example 32, the subject matter of one or any combination of Examples 1-31 can optionally include comparing the one or more calibration values with one or more threshold values; determining the mechanical testing instrument is not suitable for use with the mechanical instrument assembly based on the comparison with of the one or more calibration values with the one or more threshold values.

In Example 33, the subject matter of one or any combination of Examples 1-32 can optionally include reading an identification parameter from the memory device coupled with the mechanical testing instrument; comparing the identification parameter with an identification threshold; and precluding operation of a system including the mechanical testing instrument if the identification parameter does not meet the identification threshold.

CONCLUSION

In the foregoing description, the subject matter has been described with reference to specific exemplary examples. However, it will be appreciated that various modifications and changes may be made without departing from the scope of the present subject matter as set forth herein. The description and figures are to be regarded in an illustrative manner, rather than a restrictive one and all such modifications are intended to be included within the scope of the present subject matter. Accordingly, the scope of the subject matter should be determined by the generic examples described herein and their legal equivalents rather than by merely the specific examples described above. For example, the steps recited in any method or process example may be executed in any order and are not limited to the explicit order presented in the specific examples. Additionally, the components and/or elements recited in any apparatus example may be assembled or otherwise operationally configured in a variety of permutations to produce substantially the same result as the present subject matter and are accordingly not limited to the specific configuration recited in the specific examples.

Benefits, other advantages and solutions to problems have been described above with regard to particular examples; however, any benefit, advantage, solution to problems or any element that may cause any particular benefit, advantage or solution to occur or to become more pronounced are not to be construed as critical, required or essential features or components.

The present subject matter has been described above with reference to examples. However, changes and modifications may be made to the examples without departing from the scope of the present subject matter. These and other changes or modifications are intended to be included within the scope of the present subject matter, as expressed in the following claims.

It is to be understood that the above description is intended to be illustrative, and not restrictive. Many other examples will be apparent to those of skill in the art upon reading and understanding the above description. It should be noted that examples discussed in different portions of the description or referred to in different drawings can be combined to form additional examples of the present application. The scope of the subject matter should, therefore, be determined with reference to the appended claims, along with the full scope of equivalents to which such claims are entitled.

What is claimed is:

1. A mechanical testing assembly configured for sub-micron scale mechanical testing comprising:
   a mechanical testing instrument having one or more mechanical characteristics with values unique to the mechanical testing instrument, the mechanical testing instrument configured for installation with and use by the mechanical testing assembly; and
   a memory device incorporated with the mechanical testing instrument, wherein
      in a first condition the memory device includes one or more calibration values based on the one or more mechanical characteristic values that are unique to the mechanical testing instrument, and
      in a second condition the memory device is configured to include a failure to recognize value based on comparison of the one or more calibration values with one or more threshold values, the failure to recognize value when read by the mechanical testing assembly precludes recognition of the mechanical testing instrument and corresponding future use of the mechanical testing instrument by the mechanical instrument assembly configured to otherwise use the mechanical testing instrument.

2. The mechanical testing assembly of claim 1, wherein the mechanical testing instrument includes one or more of a probe tip, a transducer assembly and an imaging scanner assembly.

3. The mechanical testing assembly of claim 1, wherein the one or more mechanical characteristics includes a tip shape of a probe tip.

4. The mechanical testing assembly of claim 3, wherein the one or more calibration values includes an area function based on the tip shape.

5. The mechanical testing assembly of claim 1, wherein the mechanical testing instrument includes a transducer assembly and the one or more mechanical characteristics includes a spring constant of a deflectable support element coupled between a transducer and a transducer body.

6. The mechanical testing assembly of claim 1, wherein the mechanical testing instrument includes a transducer and the one or more mechanical characteristics include at least one of transducer capacitor plate area and separation between plates.

7. The mechanical testing assembly of claim 6, wherein the one or more calibration values includes the relation between voltage applied to the transducer and force applied by the transducer.

8. The mechanical testing assembly of claim 1, wherein the mechanical testing instrument includes an imaging scanner assembly including a transducer and the one or more mechanical characteristics include at least one of transducer capacitor plate area and separation between plates of the transducer.

9. The mechanical testing assembly of claim 8, wherein the one or more calibration values includes the relation between x-y lateral displacement of the transducer and voltage change at the transducer.

10. The mechanical testing assembly of claim 8, wherein the one or more calibration values includes the relation between z displacement of the transducer and voltage change at the transducer.

11. The mechanical testing assembly of claim 1 comprising a mechanical instrument assembly, and the mechanical testing instrument is installed with and used by the mechanical instrument assembly;
   wherein the mechanical instrument assembly is configured to read the one or more calibration values and the mechanical instrument assembly is configured for calibration according to the one or more calibration values for sub-micron scale mechanical testing, and the mechanical instrument assembly is configured to read the failure to recognize value of the mechanical testing instrument, and the mechanical instrument assembly precludes use of the mechanical testing instrument upon reading the failure to recognize value.

12. The mechanical testing assembly of claim 1, wherein the memory device consists essentially of one or more of a radio frequency identification chip, a wired memory chip, an inductive memory chip, a bar code, visual characters capable of optical character recognition.

13. A method of calibrating a mechanical instrument assembly comprising:
   reading a memory device incorporated with a mechanical testing instrument, the mechanical testing instrument having one or more mechanical characteristics with values unique to the mechanical testing instrument, and reading includes reading of one or more calibration values based on the one or more mechanical characteristic values;

calibrating the mechanical instrument assembly according to the one or more calibration values;

coupling the mechanical testing instrument with the mechanical instrument assembly;

conducting one or more testing operations with the mechanical instrument assembly and the mechanical testing instrument, the one or more testing operations changing at least one of the one or more mechanical characteristics;

performing analysis of the mechanical testing instrument after the one or more testing operations to update the values of the one or more mechanical characteristics based on the changes in at least one of the one or more mechanical characteristics;

writing over or appending the one or more calibration values on the memory device with updated calibration values based on the updated values of the one or more mechanical characteristics;

comparing the one or more calibration values with one or more threshold values; and determining the mechanical testing instrument is not suitable for use with the mechanical instrument assembly based on the comparison with of the one or more calibration values with the one or more threshold values.

14. The method of claim 13 comprising:

comparing the updated calibration values with one or more threshold values;

determining the mechanical testing instrument is not suitable for use with the mechanical instrument assembly based on the comparison of the updated calibration values with the one or more threshold values.

15. The method of claim 13, wherein reading the memory device includes reading the memory device with the mechanical instrument assembly, wherein the mechanical instrument assembly is configured to couple with the mechanical testing instrument and operate the mechanical testing instrument.

16. The method of claim 13, wherein reading the memory device incorporated with the mechanical testing instrument includes reading the memory device incorporated with a probe tip, and the one or more mechanical characteristics includes a tip shape of the probe tip.

17. The method of claim 13, wherein calibrating the mechanical instrument assembly according to the one or more calibration values includes calibrating the mechanical instrument assembly according to an area function based on a tip shape, wherein the area function relates an indentation depth with a cross sectional area of a probe tip included with the mechanical testing instrument.

18. The method of claim 13, wherein reading the memory device incorporated with the mechanical testing instrument includes reading the memory device incorporated with a transducer assembly, and the one or more mechanical characteristics includes a spring constant of a deflectable support element coupled between the transducer and a transducer body.

19. The method of claim 18, wherein calibrating the mechanical instrument assembly according to the one or more calibration values includes calibrating the mechanical instrument assembly with the spring constant of the deflectable support element.

20. The method of claim 13, wherein reading the memory device incorporated with the mechanical testing instrument includes reading the memory device incorporated with a transducer assembly, and the one or more mechanical characteristics includes at least one of transducer capacitor plate area and separation between plates of a transducer.

21. The method of claim 20, wherein calibrating the mechanical instrument assembly according to the one or more calibration values includes calibrating the mechanical instrument assembly with a relation between displacement of the transducer and voltage change at the transducer based on one or more of transducer capacitor plate area and separation between plates of the transducer.

22. The method of claim 13, wherein reading the memory device incorporated with the mechanical testing instrument includes reading the memory device incorporated with an imaging scanner assembly, and the one or more mechanical characteristic includes at least one of transducer capacitor plate area and separation between capacitor plates of a transducer.

23. The method of claim 22, wherein calibrating the mechanical instrument assembly according to the one or more calibration values includes calibrating the mechanical instrument assembly with a relation between x-y lateral displacement of the transducer and voltage change at the transducer based on one or more of transducer capacitor plate area and separation between capacitor plates of the transducer.

24. The method of claim 13 comprising:

reading an identification parameter from the memory device incorporated with the mechanical testing instrument;

comparing the identification parameter with an identification threshold; and precluding operation of a system including the mechanical testing instrument if the identification parameter does not meet the identification threshold.

25. The method of claim 24 comprising writing a failure to recognize value to the memory device incorporated with the mechanical testing instrument.

* * * * *